United States Patent [19]

Smits

[11] Patent Number: 5,111,811
[45] Date of Patent: May 12, 1992

[54] CARDIOVERSION AND DEFIBRILLATION LEAD SYSTEM WITH ELECTRODE EXTENSION INTO THE CORONARY SINUS AND GREAT VEIN

[75] Inventor: Karel F. A. A. Smits, KL Oirsbeek, Netherlands

[73] Assignee: Medtronic, Inc., Minneapolis, Minn.

[21] Appl. No.: 499,141

[22] Filed: Mar. 26, 1990

Related U.S. Application Data

[60] Division of Ser. No. 408,466, Sep. 18, 1989, abandoned, which is a continuation of Ser. No. 220,642, Jul. 18, 1988, abandoned, which is a division of Ser. No. 925,030, Oct. 30, 1986, Pat. No. 4,744,952, which is a division of Ser. No. 746,694, Jun. 20, 1985, Pat. No. 4,641,656.

[51] Int. Cl.⁵ .............................................. A61N 1/39
[52] U.S. Cl. .................... 128/419 D; 128/786
[58] Field of Search ............... 128/419 D, 419 P, 786, 128/785

[56] References Cited

U.S. PATENT DOCUMENTS 4,422,460  12/1983  Pohndorf ........................... 128/786
4,727,877  3/1988  Kallok ............................ 128/419 D

*Primary Examiner*—Lee S. Cohen
*Assistant Examiner*—Kennedy J. Schaetzle
*Attorney, Agent, or Firm*—Reed A. Duthler

[57] ABSTRACT

A cardioversion and defibrillation lead system and a method of use of the lead system for applying energy to the heart. The lead system and method of application are designed to maximize the efficiency of electrical energy and depolarizing the cells of the heart by equalizing current distribution across the heart and concentrating current in the muscular areas of the heart. The method of use of the lead system includes properly locating the electrodes, and applying pulses to the electrodes in one of several pulse regimes.

9 Claims, 9 Drawing Sheets

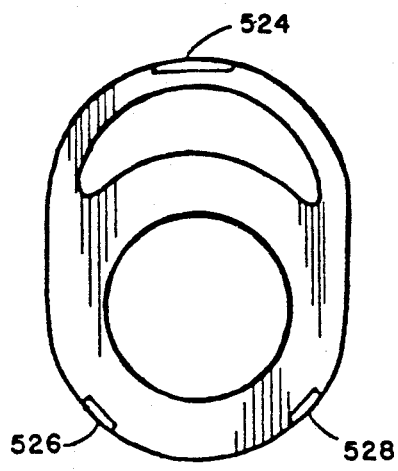
FIG. 28
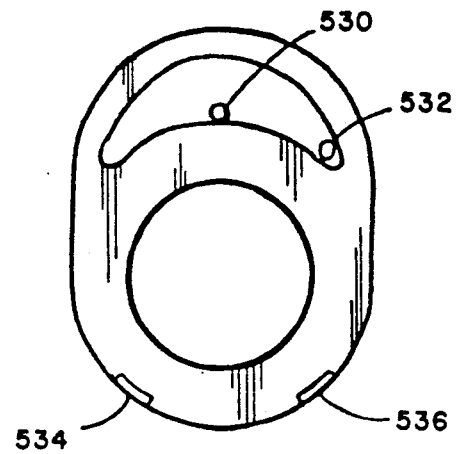
FIG. 29
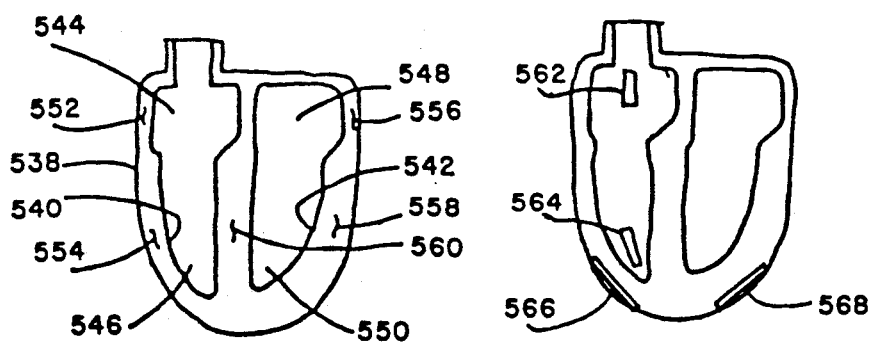
FIG. 30
FIG. 31

CARDIOVERSION AND DEFIBRILLATION LEAD SYSTEM WITH ELECTRODE EXTENSION INTO THE CORONARY SINUS AND GREAT VEIN

This application is a division of copending application Ser. No. 07/408,466, filed Sep. 18, 1989, now abandoned, which in turn is a file wrapper continuation of copending application Ser. No. 07/220,642, filed Jul. 18, 1988, now abandoned, which in turn was a divisional of copending application Ser. No. 925,030, filed on Oct. 30, 1986, now U.S. Pat. No. 4,744,952, which in turn was a divisional application of the original parent case, application Ser. No. 746,694, filed Jun. 20, 1985, now U.S. Pat. No. 4,641,656.

BACKGROUND OF THE INVENTION

This invention pertains to medical electrical pulse generators and electrical leads generally and more particularly to cardioversion and defibrillation leads and lead systems.

It has been known for many years that ventricular fibrillation, an often fatal arrhythmia, can be terminated by means of application of high energy electric current to the heart. Originally, this defibrillation current was applied to the patient by means of chest paddles in conjunction with a line powered, external defibrillator. While this method has been and most likely will continue to be the primary mode of defibrillation in the emergency room, it has been recognized that it is desirable to construct a totally implantable defibrillation system which is capable of detecting the onset of fibrillation and defibrillating the patient without the often fatal delay involved in getting the patient to an external defibrillation device.

It is known that by applying the electrical current directly to the heart, such as during open heart surgery, the amount of energy required to defibrillate the heart can be dramatically reduced. Typically, this type of defibrillation is accomplished with reduced size defibrillation paddles placed one each on the left and right ventricle of the heart. For example, in U.S. Pat. No. 2,985,172, issued to W. C. Jones, use of two paddle shaped mesh electrodes applied to the epicardium of the heart is disclosed.

An early attempt to produce an implantable electrode system for defibrillation of the heart is illustrated in U.S. Pat. No. 3,942,536 issued to Mirowski et al. In this electrode system, a single right ventricular endocardial lead is used, having one set of electrodes at its distal tip for location in the apex of the right ventricle and a second set of electrodes spaced from the set of electrodes on the distal tip a sufficient distance to place them in the superior vena cava. Other endocardial ventricular defibrillation lead systems are illustrated in U.S. Pat. No. 3,857,398 issued to Rubin and in U.S. Pat. No. 4,355,646 issued to Kallok.

In the recent past, it has been determined that the power required to defibrillate the human heart using a lead system such as described in the above patents, while significantly less than that required by the use of an external defibrillator, is still sufficiently large to make construction of a battery powered fully implantable defibrillator difficult. In addition, the relatively small surface area of the endocardial electrodes can result in extremely high current densities in the immediate vicinity of the electrodes, during application of the defibrillation pulse. This factor is important because the possibility of tissue damage increases as current density increases, and an endocardial defibrillation pulse is typically orders of magnitude greater than a typical cardiac pacing pulse.

In an attempt to create an improved defibrillation lead system, all epicardial systems have been proposed. One such is found in U.S. Pat. No. 4,030,509 issued to Heilman et al, which discloses an all epicardial system employing large surface area electrodes, one set to be applied at the apex of the heart, a second set to be applied to the atria of the heart. As an alternative, it is suggested that a superior vena cava electrode on an endocardial lead may be used in conjunction with a large electrode applied to the apex of the heart, typically referred to as an apical cup electrode.

Other large surface area electrodes for application to the human heart are disclosed in U.S. Pat. No. 4,291,707 issued to Heilman et al, which discloses electrodes fabricated of metallic mesh, sandwiched between two layers of chemically inert electrically insulative material. However, the electrodes disclosed in the Heilman applications suffer from the drawback that their surface area is essentially fixed, while, of course, the surface area of the heart to which they are sutured varies during contraction.

Recently, it has been proposed that rather than delivering electrical energy between electrodes located in the apex of the heart and electrodes located on or in the superior vena cava or atrium of the heart that a return to application of electrical energy transversely across the heart is desirable. For example, in published European patent application Publication No. 0 095 726 by the Purdue Research Foundation, it is proposed that four epicardial mesh electrodes be arranged orthogonally around the heart and that defibrillation be accomplished using two sequential orthogonal defibrillation pulses.

SUMMARY OF THE INVENTION

The present invention is directed toward the construction of a lead system having the optimum characteristics for use with an implantable cardioversion or defibrillation pulse generator. Because the pulse generator is likely to be battery powered, it is extremely desirable that the electrode system be configured to allow defibrillation or cardioversion of the heart with the minimum expenditure of energy. Increasing the efficiency of the electrode system allows an increase in the number of pulses that can be delivered before capacity of the batteries is exhausted. More importantly, by reducing the energy level applied to the heart, chances for tissue damage due to the defibrillation pulse are also reduced.

The present application discloses several configurations of lead systems developed with the purpose of maximizing the efficiency of electrical energy in depolarizing the cells of the heart, and terminating tachycardia or fibrillation. In one embodiment of the invention, the orthogonal electrode configuration of the Purdue application is utilized. However, by altering the regime for applying pulses and optimizing electrode size and placement, efficiency of the electrode system is substantially improved. A first novel pulse regime employs all four orthogonally located electrodes pulsed simultaneously during two sequential pulses. In this regime, two adjacent electrodes have positive polarity and the other two electrodes have negative polarity, concentrating defibrillation energy in the heart wall, rather than through the center of the heart. Two or more such pulses are applied, with a reverse in polarity of one pair of opposing electrodes, between each pulse. This system is referred to as the peripheral rotating pulse regime.

A second novel pulse regime for use with orthogonal electrodes is a quadripolar single pulse regime in which polarity of the four electrodes alternates with each adjacent electrode, and in which all four electrodes are used simultaneously to defibrillate the heart. This regime also concentrates energy in the heart wall. In conjunction with this pulse regime, a novel endocardial J-shaped lead is proposed. Both the peripheral rotating pulse regime and the quadripolar single pulse regime are believed to have significant advantages in efficiency over the sequential orthogonal pulse regime proposed in the Purdue application. Both the single quadripolar pulse regime and the peripheral single pulse regime may also be applied using endocardial electrodes above or in combination with epicardial electrodes.

A second embodiment of the invention provides a floating apical cup electrode for use in conjunction with the prior art bipolar endocardial defibrillation and cardioversion lead disclosed in U.S. patent application Ser. No. 4,355,646, cited above. This floating cup lead improves the current distribution within the heart, and increases the efficiency of the bipolar endocardial lead significantly. In conjunction with this floating cup electrode and with the orthogonal epicardial electrodes discussed above, a novel epicardial lead structure is proposed which provides greater ability to conform to the surface of the heart while beating. Provision of perforations within the electrode structure allow the various portions of the electrode to move relative to one another, within the plane generally defined by the electrode and allowing the electrode to conform to the compound curves of the epicardium. A somewhat different application of this principle allows for the construction of an improved apex cup electrode. These new electrode structures are believed to be substantial improvements over the epicardial leads disclosed in the Heilman patents and in the Purdue publication.

A third embodiment of the invention takes advantage of improved current distribution due to the use of two adjacent electrodes of common polarity to allow design of bipolar lead systems using the improved leads discussed above.

The objectives and advantages of the present invention will be better understood in conjunction with the following drawings and description.

BRIEF DESCRIPTION OF THE DRAWINGS

FIGS. 28 illustrates a simulated lead system employing a large surface right ventricular epicardial lead in conjunction with two left ventricular epicardial leads arranged to deliver a bipolar pulse across a simulated transverse cross section of the human heart.

FIGS. 29 illustrates a simulated lead system employing a right ventricular endocardial lead having a generally straight configuration in conjunction with two left ventricular epicardial leads, arranged to deliver a bipolar pulse, across simulated transverse cross sections of the human heart.

FIG. 30 illustrates a simulated longitudinal cross section through a human heart.

FIG. 31 illustrates a simulated lead system employing a bipolar ventricular endocardial lead with and without a floating cup electrode, across a simulated longitudinal cross section of the human heart.

DETAILED DESCRIPTION OF THE PREFERRED EMBODIMENTS OF THE INVENTION

Figure 1:
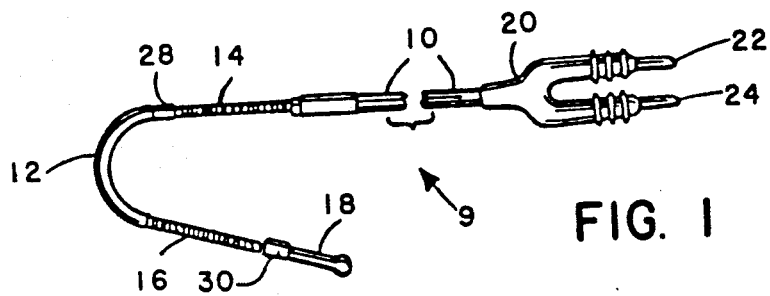
FIG. 1 is a plan view of a J-shaped ventricular endocardial lead.

FIG. 1 is a plan view of a J-shaped ventricular endocardial lead 9. The lead is provided with an elongated insulative lead body 10 which takes the form of a bend 12 in the area of its distal end. Located immediately proximal to the bend 12 is an elongated coil electrode 14. Immediately distal to bend 12 is a second elongated coil electrode 16. Coil electrodes 14 and 16 may be fabricated using close wound conductive coils, mounted exterior to elongated insulative sheath 10, or may be fabricated according to the teachings of U.S. Pat. No. 4,161,952 issued to Kinney, incorporated herein by reference in its entirety. At the distal tip of the lead is located an additional electrode 18, which may be used for monitoring functions. At the proximal end of the lead is a connector assembly 20 which bears two connector pins 22 and 24. Pin 22 is coupled to electrodes 14 and 16, and pin 24 is coupled to electrode 18 by means of elongated electrical conductors within insulative lead body 10. Assisting in location of the lead within the human heart are two sets of tines 28 and 30, which may be fabricated according to the teachings of U.S. Pat. No. 3,902,501, issued to Citron et al. By providing a J-shaped bend, a large surface area electrode can be introduced into the ventricle with reduced risk of ventricular perforation. This is particularly valuable in defibrillation and cardioversion leads because the large surface area electrodes typically display a reduced flexibility as compared to the lead body. The J-shape of the lead reduces the chances of perforation in two ways. First, because it provides increased length over which the electrodes may be mounted, it allows a thinner, more flexible lead which still displays large surface area electrodes. In addition, the J-shaped bend allows the force that the lead applies to the apex of the right ventricle to be distributed over a greater area.

Figure 2:
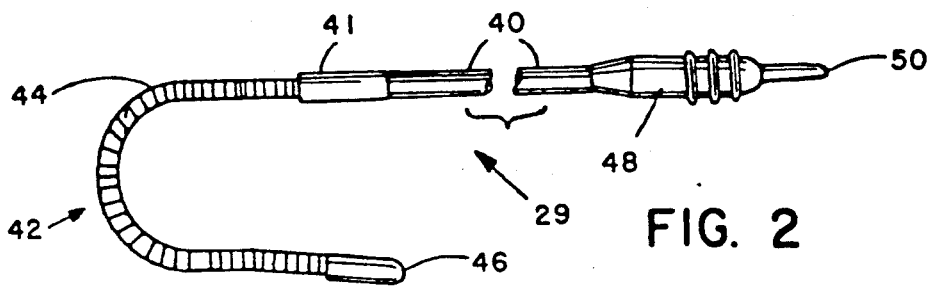
FIG. 2 is a plan view of a second embodiment of a J-shaped ventricular endocardial lead.

FIG. 2 shows a plan view of a second embodiment of a J-shaped ventricular endocardial lead 29. The lead is provided with an elongated insulative lead body 40, and includes a bend 42 in the vicinity of the distal end of the lead. Extending from a point proximal to J-shaped bend 42 to a point distal to bend 42 is an elongated electrode 44, which may be fabricated similarly to electrodes 14 and 16 shown in FIG. 1 above. At the distal end of the lead is located a rounded tip 46 which may be either conductive or nonconductive. It is important to note that because the diameter of the distal end 41 of sheath 40 is larger than the diameter of electrode 44, electrode 44 and sheath 41 meet at a 90° angle which reduces current density at that point as compared with more typical configurations in which the electrode and sheath which meet at a 180° angle. Similarly, tip 46, if non-conductive, also defines such a 90° angle. All endocardial leads illustrated in FIGS. 1-5 and 10 preferably display such a 90° angle at the electrode-sheath junction. AT the proximal end of the lead is a connector 48 bearing a connector pin 50 which is coupled to electrode 44 by means of an elongated conductor within insulative lead body 40.

Figure 3:
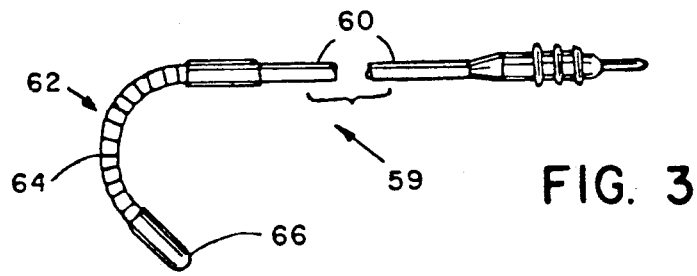
FIG. 3 is a plan view of a third embodiment of a J-shaped ventricular endocardial lead.

FIG. 3 shows a third embodiment of a J-shaped ventricular endocardial lead 59, similar to that of FIG. 2. The lead is provided with an elongated insulative lead body 60 which includes a bend 62 in its distal region. Unlike the lead of FIGS. 1 and 2, the lead of FIG. 3 does not extend distal to bend 62, but instead terminates at the distal end of bend 62. The coiled electrode 64, unlike electrode 44 (FIG. 2) extends only from the proximal end of bend 62 until the end of the lead, and does not extend to the generally straight portion of elongated insulative lead body 60. The lead is provided with a rounded distal tip 66, which may be conductive or nonconductive. Electrode 64 is designed to have a maximal surface area in the apex of the heart as close as possible to the left ventricle. As such, the electrode 64 is limited to the curved portion of the lead. This electrode, like that of FIGS. 1 and 2 above, also has the advantage that the J-shaped bend of the distal end reduces the chances of ventricular perforation.

Figure 4:
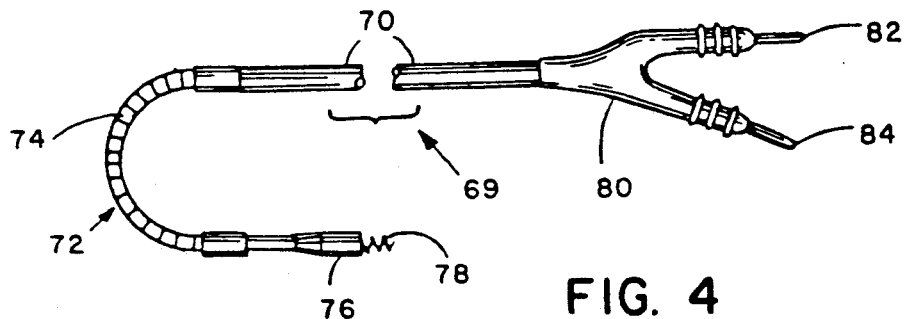
FIG. 4 is a plan view of a J-shaped, active fixation atrial endocardial lead.

FIG. 4 shows a plan view of an atrial endocardial lead 69, employing an active fixation means. The lead is provided with an elongated insulative lead body 70, and takes the form of a bend 72 in the vicinity of its distal end. The lead is provided with a coiled electrode 74 extending over the bend 72. At its distal end, the lead is provided with a fixation assembly 76, bearing a rotatable corkscrew electrode 78, which may be manufactured according to the teachings of U.S. Pat. No. 4,106,512 issued to Bisping, or U.S. Pat. No. 4,311,153 issued to Karel Smits, incorporated herein by reference in its entirety. At the proximal end of the lead is a connector assembly 80, bearing two connector pins 82 and 84 coupled to electrodes 74 and 78, respectively. Rotation of connector pin 84 rotates a coiled conductor within insulative lead body 70, to rotate fixation helix 78 distally out of fixation assembly 76, as discussed in the above cited Bisping patent.

Figure 5:
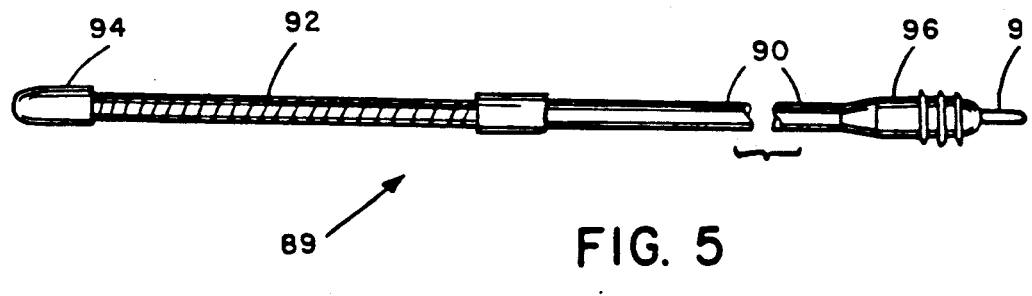
FIG. 5 is a plan view of a ventricular endocardial lead having a generally straight configuration.

FIG. 5 illustrates a ventricular endocardial lead 89 having a generally straight configuration. In construction, the lead is similar to the leads of FIGS. 2 and 3, with the exception that it is not provided with a bend. The lead is provided with an elongated insulative sheath 90, and bears a coiled electrode 92 in the vicinity of its distal end. The lead is provided with a rounded distal tip 94 which may be conductive or insulative, and bears a connector 96 at its proximal end having a pin 98 coupled to electrode 92 by means of a conductor within insulative lead body 90.

Figure 6A:
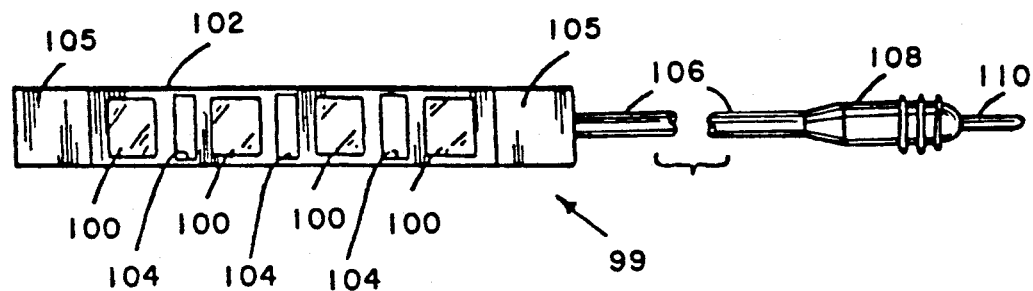
FIG. 6A is a plan view of a ventricular epicardial lead.

FIG. 6A shows a plan view of an epicardial ventricular lead 99. The lead is provided with a plurality of electrodes 100, adapted for contacting the epicardium of a human heart. The electrodes 100 are mounted in a flexible sheet 102, which is provided with apertures 104, which separate the individual electrodes 100. Electrodes 100 are interconnected electrically by means of coiled conductors running between electrodes 100, within sheet 102. Apertures 104 allow for movement of electrodes 100 relative to one another within the plane generally defined by sheet 102 as the heart contracts. Of course, as mounted to the heart, the plane defined by sheet 102 is itself curved. It is important that apertures 104 be large enough that the portions of sheet 102 which interconnect the electrodes are highly flexible members. Flexibility is enhanced by increasing the axial length of apertures 104. Suture pads 105 provide a convenient means for attaching the lead to the heart. Electrodes 100 are coupled to an implantable pulse generator by means of insulated conductor 106 which terminates in a connector assembly 108 bearing a connector pin 110 which is adapted to be coupled to a pulse generator. The structure of lead 99, shown in FIG. 6A, is believed to be particularly beneficial in an epicardial lead because it allows the lead to conform to the surface of the heart during the complex wringing motion made by the heart, during contraction.

Figure 6B:
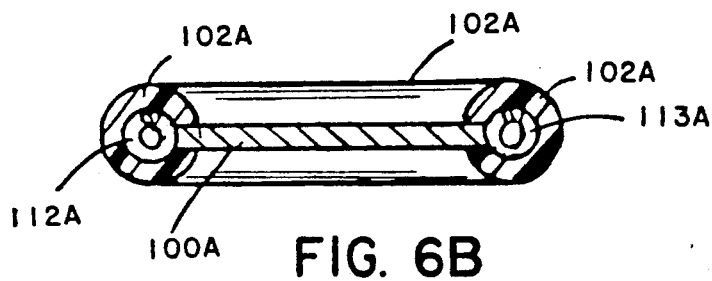
FIG. 6B is a cross sectional view of a first configuration of the lead of FIG. 6A.

FIG. 6B shows a cross sectional view of a first construction of the lead 99 shown in FIG. 6A. In this particular embodiment, electrode 100A takes the form of a metal plate, surrounded by sheet 102A which allows electrode 100A to be exposed on both front and back sides of sheet 102A. As will be discussed below, in some applications, it appears that employing epicardial electrodes of this sort may be preferential to use of electrodes in which the back surfaces of the electrodes 100A are fully insulated. Coil conductors 112A and 113A are shown in cross section, mounted within insulative sheet 102A, and are coupled to electrode 100A by welding, soldering, or other convenient method of attachment.

Figure 6C:
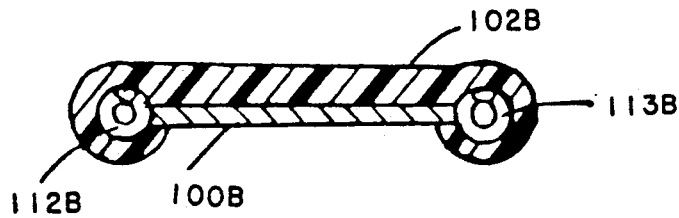
FIG. 6C is a cross sectional view of a second configuration of the lead of FIG. 6A.

FIG. 6C shows a cross sectional view of a second embodiment of the lead shown in FIG. 6A. In this embodiment, electrode 100B also takes the form of a metal plate. However, in this embodiment, insulative sheet 102B extends to cover the back side of plate 100B. Conductors 112B and 113B correspond to the similarly numbered conductors in FIG. 6B.

Figure 7:
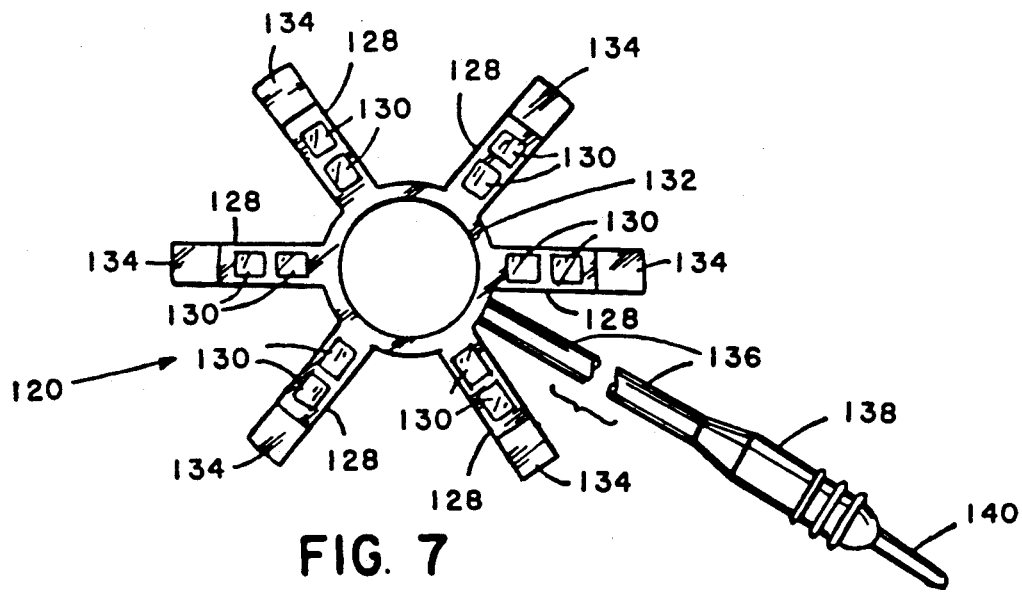
FIG. 7 is a plan view of an epicardial apex cup lead.

In both FIGS. 6B and 6C, it is important to note that sheets 102A and 102B define roughly 90° angles with electrode plates 100A and 100B, respectively. This is valuable in reducing the high current density at the edge where the electrode meets the insulation material FIG. 7 shows a plan view of an epicardial apex cup lead 120 for use with cardioversion and defibrillation lead systems. The cup consists of a central, ring shaped member 132, which bears several radiating electrode sheets 128, each of which terminates in a suture pad 134. Each of the flexible electrode sheets 128 may be fabricated similar to those shown in FIGS. 6A, 6B or 6C, above and bears a number of electrode surfaces 130. Preferentially, individual electrode surfaces 130 are open on both sides of the lead, as in the embodiment illustrated in FIG. 6B. Not insulating the backs of electrode surfaces 130 is believed beneficial in improving current distribution in the apex of the heart. All electrode surfaces 130 are connected in common, and may be coupled to a defibrillation pulse generator by means of elongated insulative conductor 136, which terminates in a connector 138 bearing a connector pin 140 which is coupled electrically to all electrode surfaces 130. This apex cup electrode is believed to have significant advantages over the apical cup electrodes of the prior art, for example those illustrated in U.S. Pat. No. 4,030,509 issued to Heilman et al. The apex cup of the present invention has the advantage that it can conform to changes in the surface geometry of the heart during contraction. This apical cup electrode, similar to the apical cup electrodes of Heilman, defines a generally conical surface having its largest circumference at suture pads 134. Unlike the electrodes of the prior art, however, this electrode, because it is fabricated of spaced electrode sheets, allows for changes in the circumference of the base of this roughly defined cone during contraction of the heart and allows rearrangement of the spacing of the electrode sheets 128 around the surface of this roughly defined cone, in accordance with the twisting and contraction of the heart. Although circular member 132 is essentially fixed in diameter, it is located close to the extreme apex of the heart, which does not change appreciably in diameter during normal contraction of the heart.

Figure 8:
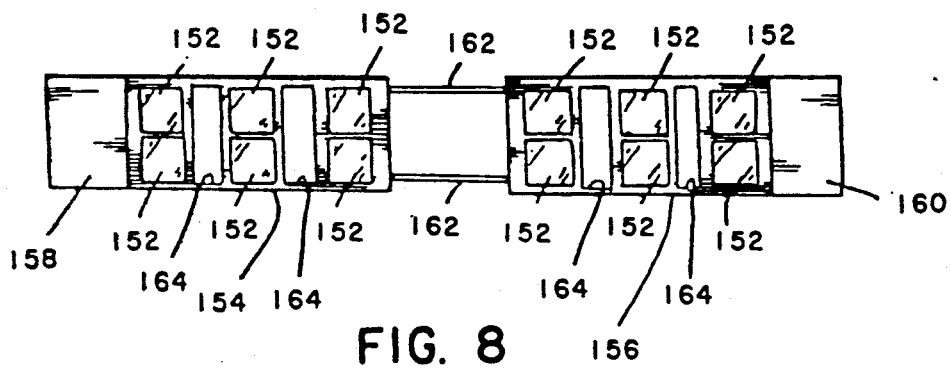
FIG. 8 is a plan view of a floating cup electrode for use on the apex of the human heart.

FIG. 8 shows a plan view of a floating cup electrode 150 for epicardial use at the apex of the heart, in conjunction with a bipolar endocardial cardioversion and defibrillation lead. The lead is similar in structure to the leads of FIGS. 6A, 6B and 6C, employing a plurality of electrodes 152. These electrodes are mounted on two flexible sheets 154 and 156 provided with suture pads 158 and 160. All of the electrodes 152 on both sheets 154 and 156 are coupled electrically in common, so that electrical currents picked up by electrodes on one sheet are delivered to the other sheet, improving the current distribution in the left ventricular wall. Flexible sheets 154 and 156 are mechanically joined by means of insulated conductors 162, which also electrically couple the electrodes 152. As in the leads of FIG. 6 and 7, each of the flexible sheets is provided with apertures 164 intermediate the electrodes 152, to facilitate the conforming of the electrodes to the changing topography of the epicardium of the human heart during contraction.

Figure 9:
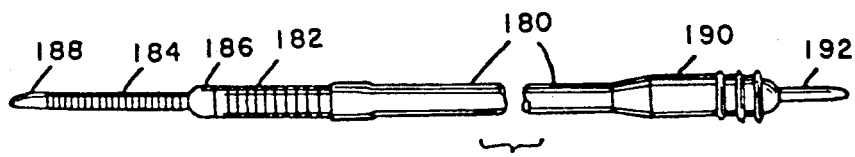
FIG. 9 is a plan view of an endocardial lead for use in the coronary sinus of the human heart.

FIG. 9 shows a plan view of an endocardial lead 170 for use in the coronary sinus. This lead is provided with an elongated insulative lead body 180, which bears two elongated coil electrodes 182 and 184 in the vicinity of its distal end. These electrodes may be constructed similarly to those shown in FIGS. 1–5. Intermediate electrodes 182 and 184 is an insulative shoulder 186. The lead is provided with a pliant, nonconductive distal tip 188, which facilitates insertion of the lead into the coronary sinus. At the proximal end of the lead is a connector 190 bearing a connector pin 192 coupled to electrodes 182 and 184. The lead presents a generally tapered profile with the diameter of electrode 184 less than that of electrode 182. This configuration is believed beneficial to allow electrode 184 to be placed in the great cardiac vein, improving current distribution in the left ventricle without unduly restricting blood flow.

Figure 10:
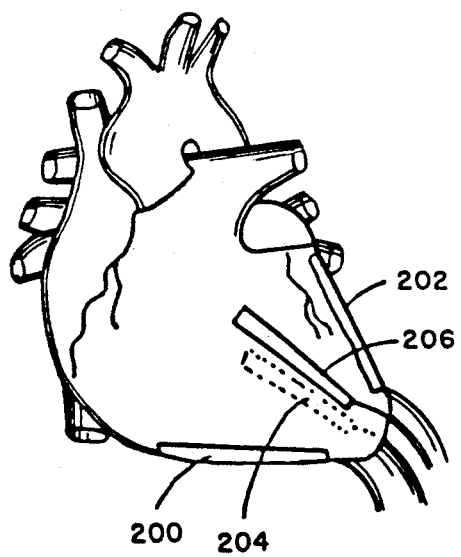
FIG. 10 shows four ventricular epicardial leads in an orthogonal configuration, on a human heart.

FIG. 10 shows four ventricular epicardial strip electrodes, mounted in orthogonal fashion on a human heart. Electrodes 204 and 206 are mounted so as to generally define a plane roughly parallel to the septum of the heart, while electrodes 200 and 202 are mounted to define a plane roughly perpendicular to the plane defined by electrodes 204 and 206. This general configuration is thus referred to as "orthogonal". Electrodes 200, 202, 204 and 206 may be fabricated according to FIGS. 6A, 6B or 6C, above, or may be epicardial mesh electrodes, of the sort described in European published Application Serial No. 8,310,5192.5 by Purdue Research Foundation, Publication No. 0,095,726 incorporated herein by reference in its entirety. This electrode arrangement is useful in applying both the peripheral rotating pulse stimulation regime and single quadripolar pulse regime, discussed above.

Figure 11A:
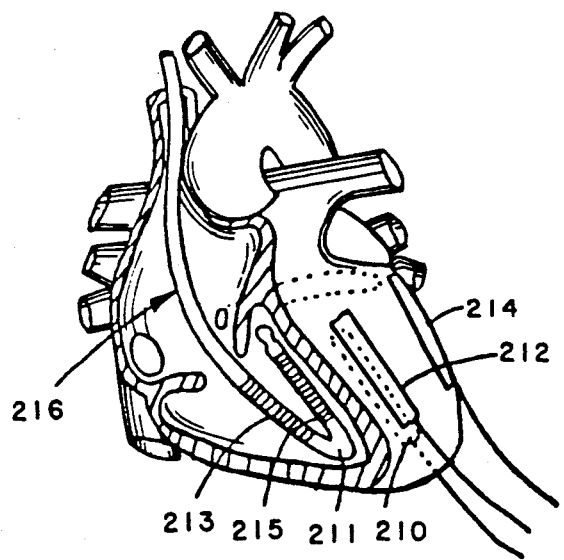
FIG. 11A shows a J-shaped ventricular endocardial lead in conjunction with three ventricular epicardial leads, arranged in an orthogonal configuration on and in a human heart.

FIG. 11A shows a cutaway view of the heart illustrating a J-shaped ventricular endocardial defibrillation lead in conjunction with three epicardial electrodes, arranged in an orthogonal fashion. In this arrangement, electrodes 210 and 212 are mounted to the left ventricular wall and are spaced roughly equidistant from the septum of the human heart. Electrode 214 is mounted approximately equidistant from electrodes 210 and 212. Endocardial J-lead 216 is mounted centered in the right ventricle. Electrodes 210, 212 and 214 may be either electrodes as illustrated in FIGS. 6A, 6B or 6C or may be electrodes similar to those discussed in the above-cited European application. Lead 216 is preferable as illustrated in FIG. 1 of the present application. In this configuration, sheath 211 is beneficial in spacing electrodes 213 and 215 away from the apex of the heart. This electrode arrangement is useful in applying both the peripheral rotating pulse regime and the single quadripolar pulse regime. In addition, this configuration may also be used to deliver a bipolar pulse in which electrodes 213 and 215 are of like polarity and electrodes 210, 212 and 214 are of like polarity, opposite that of electrodes 213 and 215.

Figure 11B:
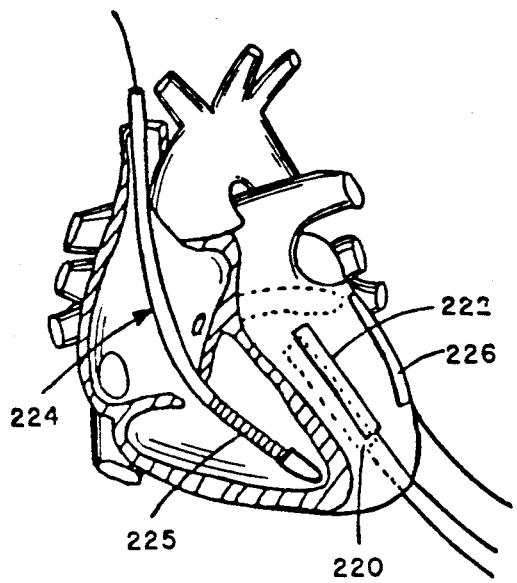
FIG. 11B shows a ventricular endocardial lead having a generally straight configuration in conjunction with three ventricular epicardial leads, arranged in an orthogonal configuration on and in a human heart.

FIG. 11B shows a cutaway view of the heart illustrating a ventricular endocardial lead having a generally straight configuration in conjunction with three epicardial ventricular electrodes, arranged in an orthogonal fashion. Epicardial electrodes 220 and 222 define a plane roughly parallel to the septum of the human heart, while electrode 225 of endocardial lead 224 and epicardial electrode 226 define a plane generally perpendicular to the plane defined by electrodes 220 and 222. Lead 224 may be fabricated according to FIG. 5. As in the case of the endocardial lead in FIG. 11A above, it is important to note that the electrode 225 of lead 224 extends for a length comparable to that of electrodes 220, 222 and 226, allowing for more even current distribution throughout the ventricular region of the human heart.

Figure 12A:
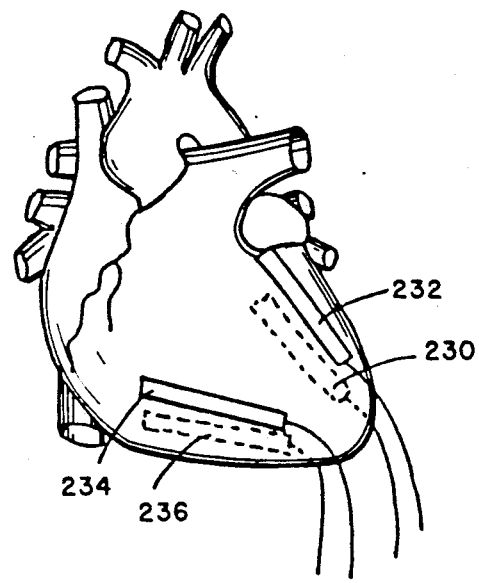
FIG. 12A shows four ventricular epicardial leads arranged in an alternate configuration on a human heart.

FIG. 12A illustrates an alternate location of four ventricular epicardial electrodes for delivery of a pulse across the heart. In this case, electrodes 230 and 232 are both mounted on the left ventricle roughly equidistant from the septum of the heart. Similarly, electrodes 234 and 236 are both mounted on the right ventricle, also roughly equidistant from the septum of the heart. This electrode arrangement, as illustrated, with electrodes 230 and 232 closely spaced and with electrodes 234 and 236 closely spaced is particularly useful in delivering a single bipolar pulse regime using all four electrodes. In this pulse regime, electrodes 230 and 232 are of like polarity and electrodes 234 and 236 are of like polarity opposite of that of electrodes 230 and 232. If electrodes 230, 232, 234 and 236 are more evenly spaced, this arrangement is believed appropriate for use with either the peripheral rotating pulse regime or the single quadripolar pulse regime.

Figure 12B:
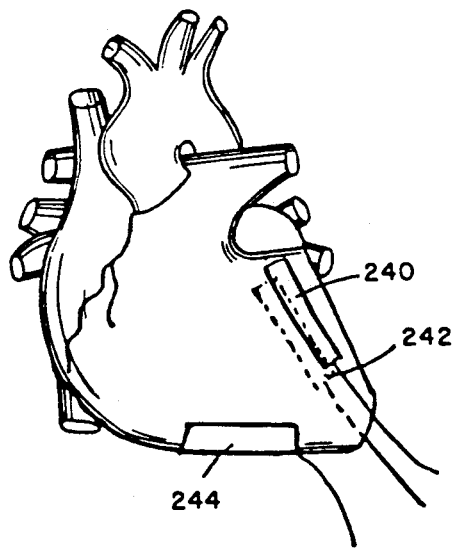
FIG. 12B shows three ventricular epicardial leads arranged on a human heart.

FIG. 12B shows an arrangement of three epicardial defibrillation electrodes arranged to deliver a pulse across the human heart. Two ventricular epicardial electrodes 240 and 242 are mounted on the left ventricle, roughly equidistant from the septum of the heart, and a third electrode 244 is mounted on the right ventricle, approximately equidistant from electrodes 240 and 242. This electrode arrangement as illustrated with electrodes 240 and 242 closely spaced on the left ventricle and electrode 244 having a surface area approximately equal to the sum of the surface areas of electrodes 240 and 242 is particularly adapted to delivery of a single bipolar pulse regime. In this regime, electrodes 240 and 242 have like polarity and electrode 244 has an opposite polarity. However, similar arrangements of three electrodes, but more evenly spaced and sized are believed useful in delivery of a peripheral rotating pulse regime.

Figure 13A:
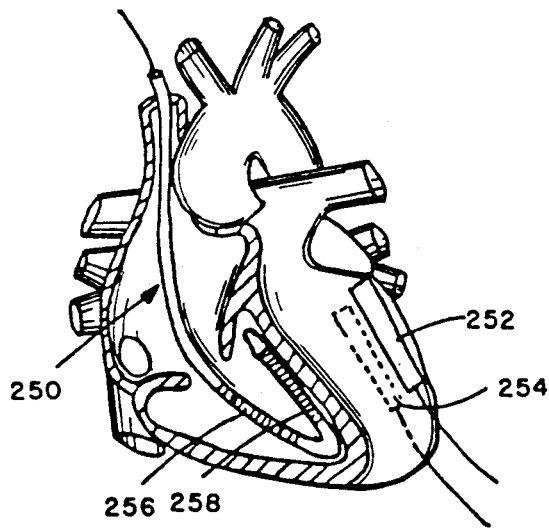
FIG. 13A shows a J-shaped ventricular endocardial lead and two ventricular epicardial leads arranged in and on a human heart.

FIG. 13A shows the combination of a ventricular J lead 250 in conjunction with two epicardial electrodes 252 and 254 arranged to deliver a pulse across the human heart. J-lead 250 is mounted in the right ventricle with the electrodes 256 and 258 lying in a plane generally parallel to the septum of the heart, while electrodes 252 and 254 are mounted on the left ventricle, roughly equidistant from the septum of the heart. This electrode arrangement is particularly adapted for delivery of a single bipolar pulse regime.

Figure 14:
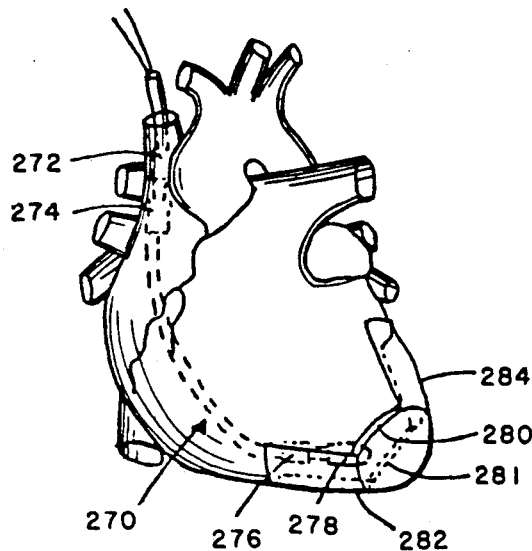
FIG. 14 shows a ventricular bipolar endocardial lead in conjunction with a floating cup electrode arranged on and in a human heart.

FIG. 14 shows an endocardial bipolar defibrillation lead 270 employing electrodes 272 and 274 located in the right atrium or superior vena cava and two electrodes 276 and 278 located in the right ventricular apex. This lead may be as described in U.S. Pat. No. 4,353,646 issued to Kallok and incorporated herein by reference in its entirety. A floating cup electrode fabricated according to FIG. 8 is mounted having one of its flexible plastic sheets 282 mounted to the right ventricle immediately exterior to the distal tip electrodes 276 and 278 of the ventricular endocardial lead 270. The other electrode sheet 284 of the floating cup electrode is mounted to the epicardium of the left ventricle. Insulated conductive wires 280 and 281 serve to both stabilize the lower ends of the floating cup with respect to the ventricle and to couple the electrodes on the two sheets. In use, the electrodes on sheet 282 located on the right ventricle pick up the electrical energy delivered by electrodes 276 and 278, and transfer it to sheet 284 on the left ventricle, improving current distribution.

Figure 15:
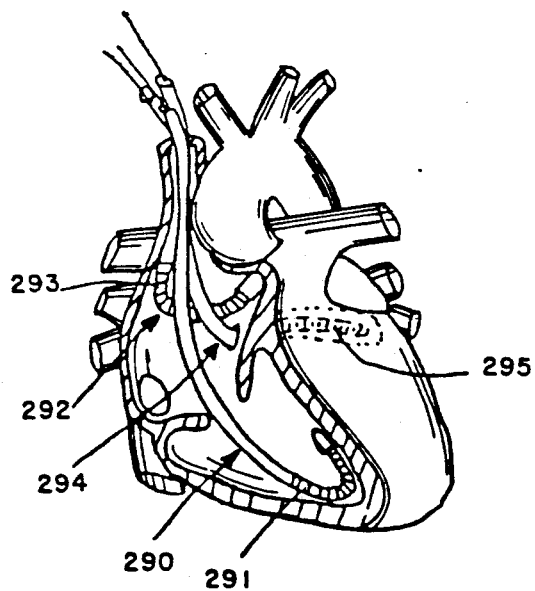
FIG. 15 shows a completely endocardial system employing a J-shaped atrial endocardial lead, a J-shaped ventricular endocardial lead, and a lead for use in the coronary sinus, arranged in a human heart.

FIG. 15 shows a cutaway view of the human heart illustrating a completely endocardial lead system. In this view, a ventricular J-shaped defibrillation lead 290 is used in conjunction with a J-shaped atrial endocardial defibrillation lead 292 and an optional coronary sinus lead 294. As illustrated, the proximal end of electrode 295 does not extend into the atrium of the heart. Lead 290 is a lead of the type illustrated in FIG. 3 in which the electrode 291 is located on the distal, curved portion of the lead, to provide as large as possible a surface area at the apex of the heart, as close as is possible to the left ventricle. This is believed desirable in an endocardial system such as this in which energy is delivered between an atrial electrode and a ventricular electrode as well as in an endocardial system in which energy is delivered between a coronary sinus electrode and a ventricular electrode because wide spacing of the apex electrode from the atrial or coronary sinus electrode is desirable. The electrode of a straight bodied lead of similar surface area would have to be located closer to electrodes 293 and 295 of leads 292 and 294 and would have a less desirable distribution of current density throughout the heart. In addition, it is difficult to locate a straight bodied lead adjacent the septum of the heart. Such a location is desirable to assure adequate current density in the left ventricular wall.

Figure 16:
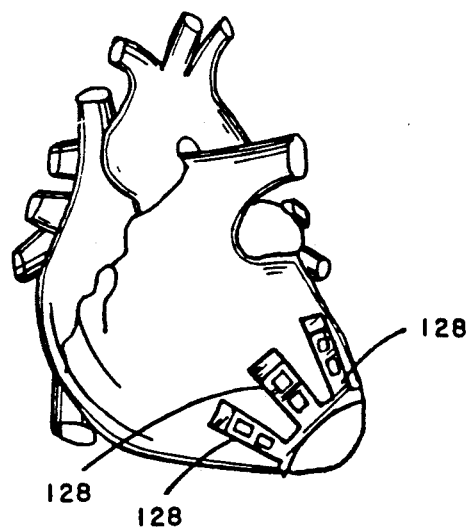
FIG. 16 shows an apex cup electrode mounted on a human heart.

FIG. 16 shows a ventricular apex cup lead of the type illustrated in FIG. 7, mounted to the apex of a human heart. In this view, it can be seen that electrode sheets 128 are arranged to define a roughly conical surface on the apex of the heart. During contraction of the heart, sheets 128 are free to move relative to one another, according to the movement of the underlying heart tissue to which they are attached.

The lead systems developed by the inventor, and the research underlying their development are based upon the understanding that the purpose of a defibrillation electrode system is to create an electrical field within the heart of appropriate strength and distribution to cause the simultaneous depolarization of a sufficient number of muscle cells within the heart to interrupt the random depolarization of heart cells known as fibrillation, and resynchronize the depolarization of the heart cells to allow for resumption of normal heart rhythm. This function is substantially different from the function of a cardiac pacing electrode which need only generate an electrical field of sufficient strength to depolarize a small number of cells adjacent to the pacing lead, with the natural propagation of heart cell depolarization within the heart resulting in propagation of a depolarization wave through heart tissue and the resultant ventricular contraction. In fibrillation, because the cells are firing in an unorganized fashion, this orderly propagation of a depolarization wave is not possible. The difference between the two situations requires that the defibrillation leads deliver amounts of energy orders magnitude higher than that of the pacing lead. This poses a particular problem for the would be developer of a practical, battery powered completely implantable defibrillation system. Even in an implantable defibrillation system employing rechargeable batteries, it is extremely desirable to maximize the efficiency of the defibrillation lead configuration and the regime for applying defibrillation pulses to the heart, to maximize effectiveness of the defibrillation pulses while minimizing electrical energy required.

In order to accomplish cardioversion of tachycardias, pulses of an energy level intermediate between that of pacing pulses and that of defibrillation pulses may be required. It is believed that the improvements in current distribution achieved by the electrode systems and pulse regimes set forth herein are also beneficial in reducing energy required to terminate tachycardias.

Based on the understanding that the ability of an electrical field to cause depolarization of a heart cell located within that field is dependent upon the current density or field strength of the field at that point, several efficiency factors can be developed. By dividing the field strength at a particular point in the heart, by the total wattage, voltage or amperage applied to the heart across the defibrillation lead set, it is possible to generate efficiency factors for power, voltage or current, which indicate the efficiency of the electrode system, at that point in the heart.

These efficiency factors also provide a method of comparing the performance of various lead systems within the heart. Looking at several theoretical models for defibrillation of the heart, we find that these three efficiency factors provide a useful method for evaluating lead performance. In case all ventricular cells must be depolarized by the defibrillation pulse or pulses, the performance of various electrode sets can be compared by comparing minimum power efficiencies found in the ventricular area. In case a certain percentage of ventricular tissue must be depolarized in order to accomplish defibrillation, it is also valuable to consider the percentage of heart tissue having minimal efficiency.

It is important, in evaluating the various lead systems, to take account of the probability that there is some minimum amount of contiguous heart tissue capable of sustaining or reinitiating ventricular fibrillation. For this reason, it is likely that the existence of small isolated areas of lower power efficiency are not likely to be detrimental to the overall performance of the electrode system.

In order to evaluate the performance of various electrode configurations and pulse application regimes, a model for simulation of current distribution across a cross section of the human heart was developed. This tank model reflects a two dimensional current distribution. The heart, of course, is a three dimensional structure. However, because most of the electrode systems disclosed employ long, narrow, roughly parallel electrodes, a two dimensional current distribution is approximated between them. This is believed to be one of the primary advantages of the use of such long, parallel electrodes, because a two dimensional current distribution has shallower current gradients than a three dimensional current distribution, and provides a more even and therefore more efficient distribution of current for defibrillation or cardioversion. In addition, it allows for the construction of a meaningful two dimensional model of current distribution through a cross section of a human heart. Because a conductive fluid displays a specific resistance inversely proportional to its fluid height, a two dimensional cross section through areas of differing resistivities can be simulated by the use of areas of conductive fluids having differing depths, layed out according to the various resistivities of the desired two dimensional cross section.

Figure 17:
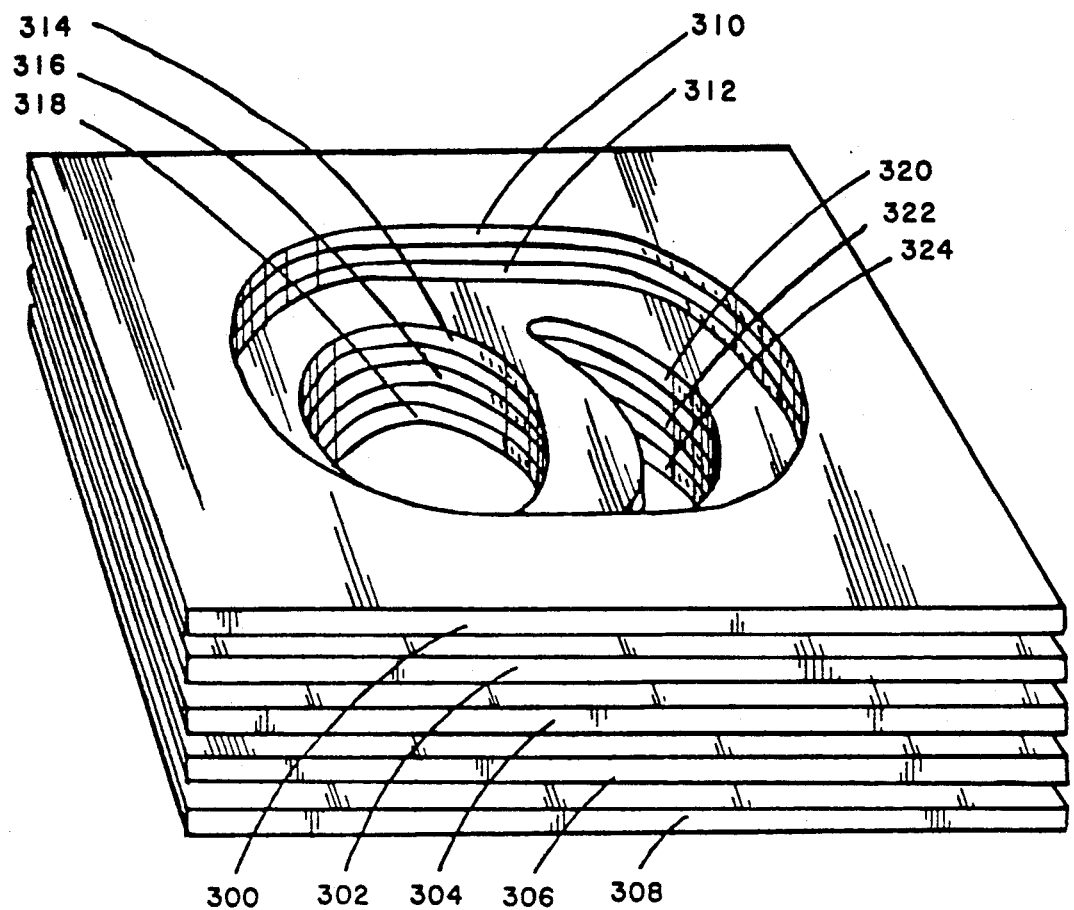
FIG. 17 shows a set of profile plates for simulation of a transverse inhomogenous cross section through a human heart, for use in a test tank.

FIG. 17 shows a set of profile plates used in conjunction with a test tank to provide a simulated inhomogenous transverse cross section through the ventricles of the human heart. Plates 300 and 302 are provided with oblong openings 310 and 312 which define the outer edge of the heart, while plates 304, 306 and 308 are provided with circular apertures 314, 316 and 318 which define the left ventricular cavity and with crescent shaped apertures 320, 322 and 324 which define the right ventricular cavity. These plates when placed in conductive fluid in the test tank provided areas of appropriately varying resistivities to simulate the blood within the ventricles, the heart tissue, and the surrounding lung tissue. A similar set of plates, not illustrated here, was used to generate a simulated inhomogenous longitudinal cross section through the human heart.

Figure 18:
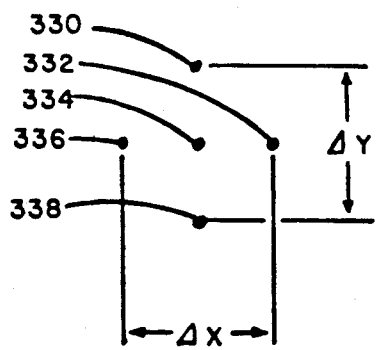
FIG. 18 shows the geometric arrangement of measurement electrodes for use in a test tank in conjunction with the profile plates of FIG. 17.
Figure 19:
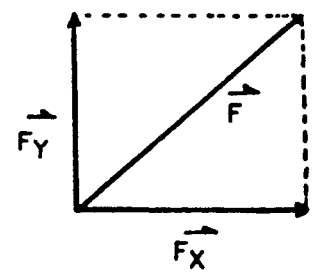
FIG. 19 shows the vector sum of the field strength vectors determined from the electrodes of FIG. 18.

In order to measure field strength at different points within the test tank, a probe bearing five electrodes arranged in the configuration indicated in FIG. 18 was employed. Electrode A, located at the center of the probe was used to determine the electrical potential at that point. Electrodes B and C define an X axis, while electrodes D and E define a Y axis. By calculating the voltage differential between electrodes B and C, over distance X between electrodes B and C, a vector field strength $F_x$ for the X axis is derived. Vector field strength $F_y$ in the Y axis is similarly determined. By adding the vector sums of the field strengths taken along the X and Y axes, as shown in FIG. 19, a composite field strength F may be derived and plotted on a simulated cross section corresponding to the profile plates of FIG. 17, at the location of electrode A. This allows the determination of lines of equal field strength which are also lines of equal current density in areas where the fluid depth is constant due to the uniform resistivity of the conductive fluid intermediate the measuring electrodes.

With calibration of the specific fluid resistivity and by dividing the measured field strength by the total wattage applied across the test electrodes in the tank, plots of power efficiency may be obtained. This test tank model was used to test the relative efficiencies of the illustrated electrode systems, and to provide an indication of ways of optimizing electrode size, location and pulse application regime for maximum efficiency.

Figure 20:
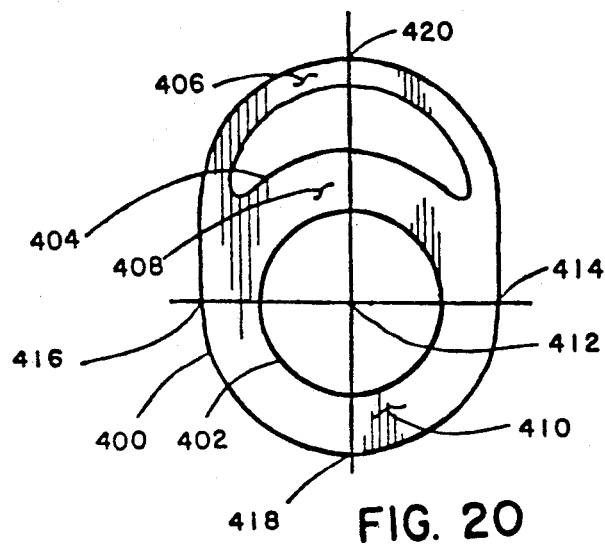
FIG. 20 illustrates a simulated transverse cross section of the human heart.

FIG. 20 shows a cross section of the human heart simulated by the test tank system described in conjunction with FIGS. 17, 18, and 19. The outer periphery of the heart 400 is simulated by oblong apertures 310 and 312 of plates 300 and 302 illustrated in FIG. 17. The crescent shaped right ventricular cavity 404 corresponds to apertures 320, 322 and 324 of plates 304, 306 and 308 of FIG. 17. The left ventricular cavity 402 corresponds to circular apertures 314, 316 and 318 of plates 304, 306 and 308 of FIG. 17. In this cross section, the heart tissue may conveniently be divided into three main areas including the right ventricular wall 406, the septum area 408 and the left ventricular wall 410. In order to be able to map the locations of various epicardial electrodes simulated in these tests, a coordinate system was assigned to the cross section using the center 412 of the left ventricle as the origin. The X axis is parallel to the septum, and intersects the periphery of the heart at points 414 and 416 which have coordinate values of (40,0) and (−40,0) respectively. The Y axis intersects the periphery of the heart at points 418 and 420 which have coordinates (0,−40) and (0,60), respectively.

Figure 21:
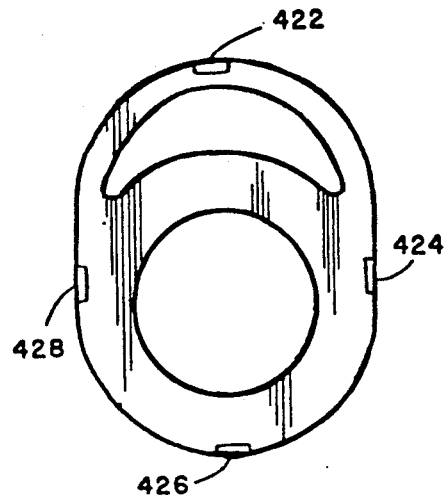
FIG. 21 illustrates a simulated orthogonal electrode system using four epicardial electrodes.

FIG. 21 shows a simulated-orthogonal electrode system. Electrodes 422, 424, 426 and 428 correspond to electrodes 200, 204, 202 and 206, respectively, of FIG. 10. This simulation was used to evaluate the sequential orthogonal pulse regime, the sequential orthogonal pulse regime, the peripheral rotating pulse regime and the single quadripolar pulse regime.

Figure 22:
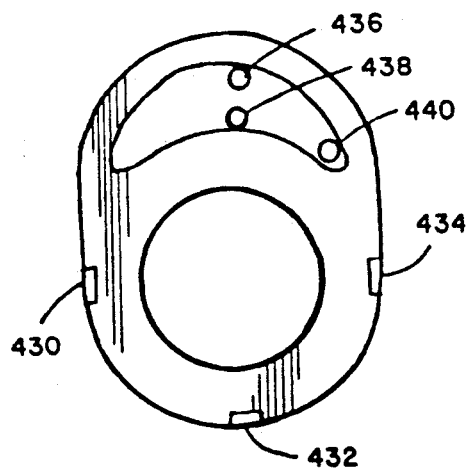
FIG. 22 illustrates a simulated orthogonal electrode system using three epicardial electrodes and an endocardial lead.

FIG. 22 shows a simulated endocardial/epicardial orthogonal lead system. Epicardial electrodes 430, 432 and 434 correspond to electrodes 222, 226 and 220, respectively, of FIG. 11B. Electrodes 436, 438 and 440 simulate electrode 225 of lead 224 shown in FIG. 11B, at three different locations within the right ventricle.

Figure 23:
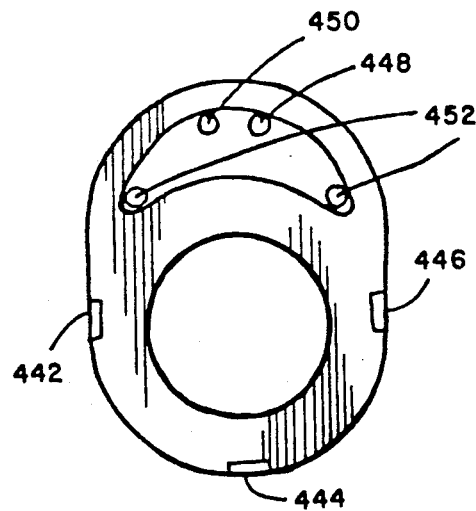
FIG. 23 illustrates a simulated orthogonal electrode system using three epicardial electrodes and a J-shaped endocardial lead.

FIG. 23 shows a second simulated endocardial/epicardial orthogonal electrode system. In this system, electrodes 422, 424 and 426 correspond to electrodes 212, 214 and 210, respectively, of FIG. 11A. Electrodes 448 and 450 correspond to electrodes 213 and 215 of lead 216 of FIG. 11A in a first location against the right ventricular wall and in an embodiment having a narrow J-shape. Electrodes 452 and 454 correspond to electrodes 213 and 215 of lead 216 with FIG. 11A, located in a second position with the electrodes located adjacent the septum, in an embodiment of the lead having a wide J-shape.

QUADRIPOLAR SINGLE PULSE REGIME

The quadripolar single pulse regime employs at least four electrodes spaced circumferentially around the ventricles of the heart, in which a defibrillating or cardioverting pulse is delivered using all electrodes. As such, this pulse regime may be delivered using the electrode system disclosed in the above cited European Patent Application Publication No. 0095726. In this pulse regime, each electrode has a polarity opposite that of both electrodes adjacent to it. As such, current can be expected to flow between all pairs of adjacent electrodes, and an area of zero current flow is expected in the center of electrode system, as no current will flow between electrodes of like polarity. This system is believed to be valuable in that it concentrates the current in the wall of the heart. In addition, appropriate location and size distribution of the electrodes places the zero current area in the blood filled left ventricle, away from muscle tissue. Finally, because all four electrodes are used simultaneously rather than two at a time, system impedance is reduced, as compared with a sequential orthogonal pulse regime employing the same electrodes. Given equal current levels applied to the electrodes, this also reduces the current density gradient in the immediate vicinity of the electrodes, reducing the possibilities of tissue damage at or around the electrodes.

The quadripolar pulse regime was tested using a simulated orthogonal, four electrode system as illustrated in FIG. 21. For each test of this pulse regime, 100 milliamps of alternating current were applied to the electrodes, with electrodes 422 and 426 in common and electrodes 428 and 424 in common. Field strengths were measured using the probe described in conjunction with FIG. 18.

In an effort to determine appropriate placement of electrodes 424 and 428, tests were taken moving electrodes 424 and 428 in parallel from a position approximately midway between electrodes 422 and 426, toward the left ventricle. Electrodes 422 and 426 were located at (0,60) and (0,−40), respectively. All electrodes were simulated using 5 mm stainless steel plates. By moving electrodes 428 and 424 to a position where the center of the left ventricle is roughly between them, the zero current area is moved away from the septal area, and into the blood filled left ventricle, improving current distribution in the area of the septum. A summary of the results of these tests is given below in Table 1, which sets forth the locations of electrodes 424 and 428, minimum power efficiencies in (volts/meter)/watt for the right ventricle (RV), septum, and left ventricle (LV), and the impedance of the electrode system.

In an effort to determine the influence of the location of the left ventricular electrode 426, tests were run moving electrode 426 from a position centered equidistant between electrodes 428 and 424, and moving electrode 426 gradually toward electrode 428. Electrodes 424 and 428 were located at (40,14) and (−40,14), respectively. All electrodes were again simulated using 5 mm plates. A summary of these results is set forth in Table 2, below, which sets forth the locations of electrode 426, along with system impedance, and minimum power efficiencies for the right ventricle, septum and left ventricle. Generally, as electrode 426 was moved toward electrode 428, field strength between those two electrodes increased, while field strength between electrodes 426 and 424 decreased. An even spacing of electrodes 424, 426 and 428 appears beneficial.

As indicated in Table 1, below, movement of electrodes 428 and 424 to a position where the center of the left ventricle is between them resulted in some reduction of field strength in the area of the right ventricular wall. In an effort to increase the field strength in the area of the right ventricular wall, tests were run increasing the size of electrode 422, relative to electrodes 424, 426 and 428. A summary of these results is shown in Table 3 below. Electrodes 424 and 428 were located at (40,0) and (−40,0) in examples A, B and C and were located at (39,−6) and (−39,−6) in examples D, E and F. Electrodes 424, 426 and 428 were simulated using 5 mm stainless steel plates, while electrode 422 was simulated using 5, 10 and 20 mm steel plates. It can be seen that by increasing the size of electrode 422 relative to the other electrodes, the field strength in the right ventricle is improved without detriment to the field strength in the septum and left ventricle. This also moves the zero current area towards the left ventricular cavity.

In summary, the quadripolar single pulse regime appears to have advantages over the sequential orthogonal pulse regime, and can be employed using a similar electrode arrangement. The efficiency of the quadripolar pulse regime can be improved by proper electrode location which places the zero current density area in the left ventricle, which may be accomplished by arranging the electrodes so that lines joining electrodes of like polarity cross at approximately the center of the left ventricle. As discussed below, this electrode arrangement also appears to be beneficial in the sequential orthogonal pulse regime and the peripheral rotating pulse regime.

As an alternative to all epicardial systems, several systems were evaluated to determine whether the single quadripolar pulse regime could be effectively applied by means of a right ventricular endocardial lead in conjunction with three left ventricular epicardial electrodes. Such a system would be advantageous in allowing fall back to an endocardial defibrillation regime of the sort set forth in U.S. Pat. No. 3,942,536, issued to Mirowski, by the simple expedient of including an electrode for location in the superior vena cava on the right ventricular endocardial lead. In addition, the low resistivity of the blood in the right ventricle may be advantageous in improving current distribution in the right ventricular and septal areas.

FIG. 22 shows a simulated endocardial/epicardial system corresponding to the system illustrated in FIG. 11B. In this system, the right ventricular endocardial lead may be a lead as illustrated in FIG. 5, or may be a lead as disclosed in U.S. Pat. No. 3,942,536 issued to Mirowski et al, cited above, employing elongated electrodes for location in the right ventricle and in the superior vena cava. For use in the quadripolar single pulse regime, only the electrode located in the right ventricle would be used. Epicardial electrodes were simulated using 5 mm stainless steel plates and the endocardial electrode was simulated using a single 3 mm diameter stainless steel rod. Results of testing various locations of the endocardial electrode, illustrated at 436, 438 and 440 are listed in Table 3 below. Electrodes 430, 432 and 434 were located at (−40,0), (0,−40) and (40,0), respectively. Results appear to be best when the electrode is located centrally within the right ventricle, either against the septal wall or the outer wall of the ventricle. However, the natural location of the electrode is as illustrated at 440, and it is believed that it would be difficult to chronically locate an endocardial electrode as illustrated at 436 or 438 of FIG. 22. Therefore, movement of electrodes 430, 432 and 434 in a generally clockwise direction to space them more evenly with respect to electrode 440 would be desirable to improve current distribution.

FIG. 23 illustrates an alternative endocardial/epicardial system employing a J-shaped endocardial defibrillation lead which may be constructed as illustrated in FIG. 1, or may also include an electrode in the superior vena cava. Electrodes 442, 444 and 446 were simulated using 5 mm stainless steel plates and were located at (−40,0), (0,−40), and (40,0), respectively. Electrodes 448 and 450 were simulated using 1.3 mm diameter steel rods in Example A (Table 4). Electrodes 452 and 454 were simulated by 1.3 mm and 3 mm stainless steel rods in Examples B and C, respectively (Table 4). Testing of this configuration with a narrow J, as simulated by electrodes 450 and 448 indicates that this is probably the optimal configuration for an endocardial J-lead when used in conjunction with the three epicardial electrodes deliver a single quadripolar pulse. However, stable location of a narrow J-shaped lead centered in the right ventricle is believed to be difficult. A more natural and stable location for a J-shaped endocardial defibrillation lead is simulated by electrodes 452 and 454, which are located adjacent the septum. However, as indicated in Table 4 below, this arrangement results in a larger area of reduced current density in the septal area, and in the right ventricular area intermediate electrodes 452 and 454.

SEQUENTIAL ORTHOGONAL PULSE REGIME

The sequential orthogonal pulse regime described in the above cited Purdue application employs four epicardial electrodes, spaced around the ventricles of the heart, in which pairs of opposing electrodes are sequentially pulsed. For example, in the simulation of FIG. 21, electrodes 428 and 424 might first apply defibrillation pulse to the heart, followed by electrodes 422 and 426. Testing of this system was done using the simulation illustrated in FIG. 21, as discussed above. Results of this testing are summarized in Table 6, below. Examples A-C of Table 6 illustrate power efficiencies of the simulated sequential orthogonal pulse regime. In order to calculate power efficiencies in a two pulse system, it was assumed that the effects of individual defibrillation pulses were not cumulative to one another. Therefore, at any point in the simulated cross section, the field strength was taken as the greater field strength of the two sequential pulses. This field strength was divided by the total power applied by two sequential pulses, to give the power efficiencies set forth in Table 6. From this simulation, it appears that by arranging electrodes 428 and 424 so that the center of the left ventricle is roughly between them, improved power efficiencies can be obtained. This is beneficial, in that the same electrode arrangement appears to be valuable for use in the quadripolar single pulse regime discussed above. Therefore, this electrode arrangement can be used in a system in which the physician is given the choice of the pulse regime to apply, without unduly compromising the performance of either system.

PERIPHERAL ROTATING PULSE REGIME

The peripheral rotating pulse regime is a multipulse regime, employing three or more electrodes. During each pulse, at least one electrode has a like polarity to one adjacent electrode and a polarity opposite that of the other adjacent electrode, as spaced around the heart. Between successive pulses, polarities of electrodes are altered so that electrodes of like polarity in one pulse have differing polarities in the next subsequent pulse. This system was also tested using the simulation of FIG. 21. Two sequential pulses were applied across the simulated cross section. For example, during the first pulse, electrodes 422 and 424 might be positive and electrodes 426 and 428 negative. During the second pulse, electrodes 426 and 424 would be positive and electrodes 428 and 422 would be negative. During the first pulse, therefore, current would be concentrated between electrodes 422 and 428 and between electrodes 424 and 426. The zero current areas between electrodes 422 and 424 and between electrodes 428 and 426 appeared as expected. However, the simulation indicated that rather than being spaced directly between each pair of electrodes of like polarity, they were moved outward, by the influence of the electrode pair of opposite polarity.

In testing and simulation, only two sequential pulses were used. However, it may also be beneficial to continue application of pulses for a number of pulses equal to the number of electrodes so that each electrode has had both positive and negative polarities twice, and each area of the heart has been twice located between electrodes of opposite polarities.

In order to calculate power efficiencies, the calculations used with the sequential orthogonal pulse were performed. The highest field strength at each point, during either of the two pulses was divided by the total power applied during both pulses. The results of these tests are summarized as Examples D, E and F in Table 6 below. It appears that for this regime, as well, it is beneficial to have electrodes 428 and 424 located opposite one another, approximately centered on the center of the left ventricular cavity. As such, this electrode configuration gives the physician a choice of three pulse regimes which may be applied to the heart, without having to sacrifice efficiency for the added flexibility. As indicated in Table 6, the power efficiencies of the peripheral rotating pulse system were higher than that of the sequential orthogonal pulse system. More important, however, the peripheral rotating pulse system uses all four electrodes simultaneously, resulting in a dramatic reduction in system impedance. As such, the current density gradients surrounding the individual electrodes were less steep for the peripheral rotating pulse system than for the sequential orthogonal pulse system. In addition, the voltage efficiency (field strength/voltage) is substantially greater for the peripheral rotating pulse system due to the reduced impedance of the four electrode system This is believed to be particularly beneficial in a totally implanted defibrillation system, because the voltage which can be applied to the electrode system is dependent on the high voltage circuitry used. Voltages below 350 V allow use of available small, reliable circuitry. As such, the peripheral rotating pulse system is believed to be preferable for use in an all implanted defibrillation system to the sequential orthogonal pulse regime set forth in the above cited European application.

Figure 24:
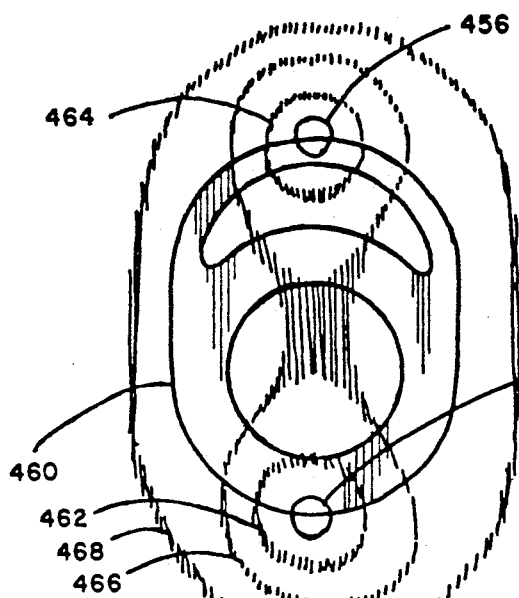
FIG. 24 illustrates a current density distribution around a single pair of electrodes applying a bipolar pulse across a simulated homogenous cross section of the heart.
Figure 25:
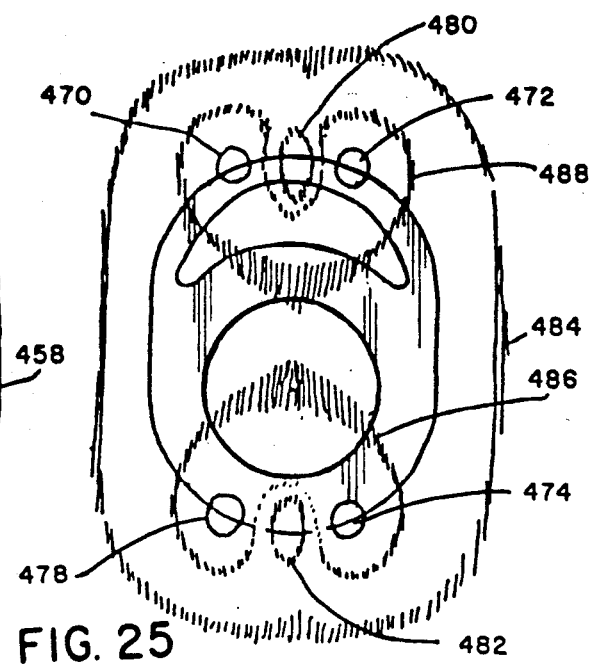
FIG. 25 shows the distribution of current densities around two pairs of epicardial strip electrodes applying a bipolar pulse across a simulated homogenous transverse cross section of the human heart.
Figure 26:
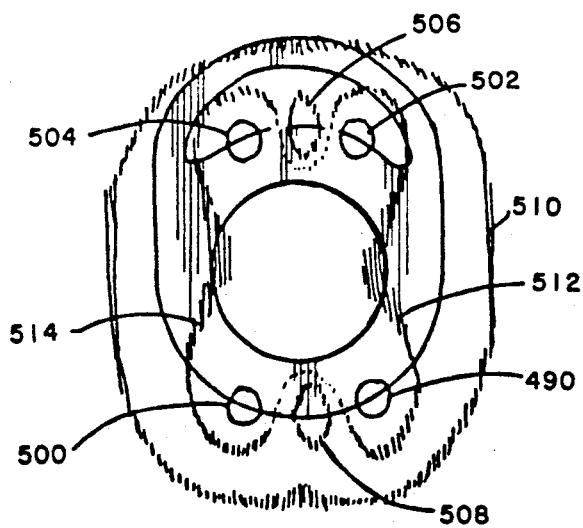
FIG. 26 shows the distribution of current densities around a ventricular J-shaped electrode in conjunction with a pair of left ventricular epicardial strip electrodes, applying a bipolar pulse across a simulated homogenous transverse cross section of the human heart.

FIGS. 24, 25 and 26 illustrate computer simulated field strength distributions around electrodes in a homogenous two-dimensional conductive field with the same voltage applied over the electrodes in each figure. For ease of understanding, simulated transverse cross sections through the heart have been superimposed on the field strength graphics. It should be kept in mind that this simulation does not take into account the differing conductivities of blood, heart tissue and lung tissue.

FIG. 24 shows the field strength distribution around a single pair of electrodes, located on the right and left ventricles of the heart. Electrodes 456 and 458, for ease of calculation, are simulated as circular, cylindrical electrodes passing through the simulated two dimensional field. The shaded areas indicate areas of identical field strength, with field strength falling by a factor of two for each shaded area moving outward from the electrodes.

FIG. 25 shows a simulation of the field strength around two pairs of electrodes, mounted to the left and right ventricle of the heart Electrodes 470 and 472, mounted to the right ventricular wall are of like polarity and electrodes 478 and 474 mounted to the left ventricular wall are of like polarity, opposite to that of electrodes 470 and 472. As would be expected, there are areas of low current density intermediate electrodes of like polarities. However, by keeping the interelectrode spacing small, is believed that this area will be sufficiently small to be unable to sustain fibrillation on its own. In this drawing, shaded areas 486 and 488 correspond in strength to shaded areas 462 and 464 of FIG. 24. Shaded areas 480, 482 and 484 correspond in strength to shaded area 466 of FIG. 24. As such, it can be seen that a system employing four electrodes arranged as shown in FIG. 25 should have a substantially improved and more even current distribution than a simple pair of electrodes mounted as shown in FIG. 24. Electrodes 470, 472, 474 and 476 of FIG. 25 correspond to electrodes 230, 232, 234 and 236 of FIG. 12A.

FIG. 26 shows the simulated field strengths around a combination endocardial/epicardial four electrode system. In this simulated cross section, electrodes 502 and 504 correspond to electrodes 256 and 258 of lead 250 in FIG. 13A. Electrodes 490 and 500 correspond to electrodes 252 and 254 in FIG. 13A. Again, there are small areas of low field strength 506 and 508 which correspond to areas 482 and 480 of FIG. 25. However, overall field strength distribution is substantially improved over the system of FIG. 24, with field strength of shaded areas 512 and 514 corresponding to the field strength of areas 462 and 464 of FIG. 24 and field strength of area 510 corresponding to field strength of area 466 of FIG. 24.

Figure 27:
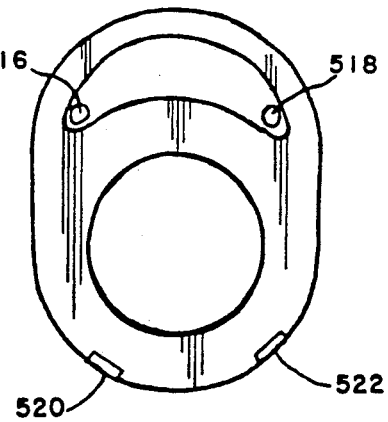
FIG. 27 illustrates a simulated lead system employing two left ventricular epicardial leads and a right ventricular J-lead to deliver a bipolar pulse, across a simulated transverse cross section of the human heart.

FIG. 27 illustrates a simulated endocardial/epicardial bipolar defibrillation system corresponding to that illustrated in FIG. 13A. Electrodes 516 and 518 are simulated by 3 mm stainless steel rods and correspond to electrodes 256 and 258 of lead 250 of FIG. 13A. Electrodes 520 and 522 are simulated by 10 mm steel plates and correspond to electrodes 252 and 254 of FIG. 13A. Test results of various spacings of electrodes 520 and 522 are set forth in Table 7, below. This system provides excellent current distribution in the left ventricle, which makes up the majority of the mass of the heart. Surprisingly, current density in the important septal area is high, with the expected zero current density area between electrodes 516 and 518 moved outward, into the right ventricular cavity due to the influence of electrodes 520 and 522. This system does have a low current area including much of the right ventricular wall, approximately centrally located between electrodes 516 and 518. In example C (Table 7), a right ventricular epicardial electrode located between electrodes 516 and 518 was added. This electrode was simulated using a 5 mm stainless steel plate and had the same polarity as electrodes 520 and 522. Addition of this electrode improved current distribution in the right ventricle at the expense of the septum. It is believed likely that an electrode system as in Examples A and B which captures the left ventricle and septum will be effective in terminating fibrillation, because the vast majority of ventricular heart tissue is located in the left ventricle.

FIG. 28 illustrates an alternative all epicardial defibrillation system for delivery of a bipolar pulse across the heart. In this figure, electrodes 524, 526 and 528 are located as illustrated, correspond to electrodes 244, 240 and 242 of FIG. 12B. Electrodes 526 and 528 are commonly charged during a defibrillation pulse. Results of tests using various sized electrodes in this configuration are given below in Table 8.

Figure 13B:
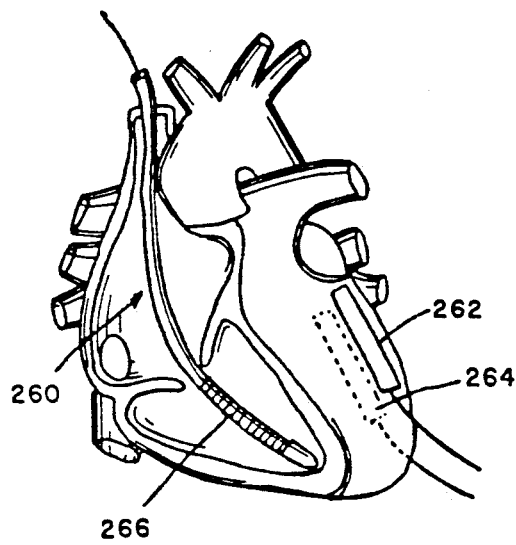
FIG. 13B shows a ventricular endocardial lead having a generally straight configuration in combination with two ventricular epicardial leads arranged in and on a human heart.

FIG. 29 illustrates an endocardial/epicardial system for applying a bipolar defibrillation pulse across the heart. In this figure, electrodes 534 and 536 are located as illustrated, correspond to electrodes 262 and 264 of FIG. 13B. Electrodes 530 and 532 show alternate locations of an electrode corresponding to electrode 266 of lead 260 of FIG. 13B. Electrodes 532 or 530 may also be ventricular electrodes on a lead as illustrated in U.S. Pat. No. 3,942,536 issued to Mirowski, cited above, which will allow use of the endocardial lead, by itself, for defibrillation in the event of failure of one or more of the epicardial leads. As illustrated in Table 9, below, the optimal placement of the endocardial electrode appears to be as illustrated at 530 in FIG. 29. However, it is believed difficult to chronically locate an endocardial lead in this position. The natural location of the lead, illustrated at 532 in FIG. 29, results in a low current area in the right ventricle if electrodes 534 and 536 are located symmetrically with respect to the left ventricle. Movement of electrodes 534 and 536 clockwise to space them, as a pair, across the left ventricle from electrode 532 substantially improves current distribution.

FIG. 30 shows a simulated longitudinal cross section of a human heart, simulated with profile plates (not illustrated) in the test tank system described in conjunction with FIGS. 17, 18 and 19 above. Appropriate profile plate apertures define the periphery of the heart 538, the interior surface 540 of the right ventricle 546 and the right atrium 544, and the interior surface 542 of the left ventricle 550 and the left atrium 548. In this view, the heart tissue can be conveniently divided into the right atrial wall 552, the right ventricular wall 554, the left atrial area 556, the left ventricular wall 558 and the septal area 560. This simulated non-homogenous longitudinal cross section was used to test the efficiency of the floating cup electrode as illustrated in FIG. 14.

FIG. 31 shows a simulated system including a bipolar endocardial lead having electrodes 562 and 564. This lead may be built according to U.S. Pat. No. 3,942,536, issued to Mirowski or as disclosed in U.S. Pat. No. 4,355,646 issued to Kallok, and illustrated in FIG. 14, above. Electrodes 566 and 568 correspond to electrode sheets 282 and 284 of the floating cup lead shown in FIG. 14, and are connected in common. Testing of this system with only electrodes 562 and 564 revealed a good current distribution in the right ventricular wall and the septal areas, but relatively poor current distribution over a large portion of the left ventricle wall. When the floating cup was added, simulated by stainless steel plates, current densities in the left ventricular wall improved substantially, without significant reduction of current density in the right ventricular or septal areas. Results from these tests are summarized in Table 10, below, which shows minimum power efficiencies for the right ventricle (RV), lower left ventricle (LLV), upper left ventricle (ULV) and septum.

The combination of the endocardial lead and the floating cup electrode is believed to be a particularly practical approach to a defibrillation electrode system. The floating cup, unlike other epicardial leads or electrodes requires no connection to the defibrillation pulse generator, and therefore has substantially reduced chances of failure. Even in the event of failure of the floating cup, the endocardial electrodes in place still may be used as a back-up system for defibrillation. In addition, the floating cup electrode can be added to improve the efficiency of endocardial defibrillation systems already in place, which may be difficult to remove or reposition due to fibrotic growth. Thus, the floating cup electrode provides a valuable opportunity for improving endocardial defibrillation systems.

The floating cup may be especially useful for application with cardioversion of ventricular or reentrant tachycardias with left ventricular origin. The physician can mount the left ventricular electrode sheet over the ectopic focus which is origin of the tachycardia resulting in more efficient delivery of cardioverting energy to the origin. The origin can be detected by complex EKG analysis or by direct threshold measurements using a test probe.

TABLE 1

| | Location of 424, 428 | Impedance (ohms) | Min. Power Efficiency (V/m)/Watt | | |
|---|---|---|---|---|---|
| | | | RV | Septum | LV |
| A | ±40, 14 | 216 | 15.3 | 8.9 | 12.1 |
| B | ±40, 4 | 231 | 11.0 | 10.9 | 16.8 |
| C | ±40, 0 | 231 | 11.0 | 10.9 | 16.8 |
| D | ±39, −6 | 231 | 9.6 | 10.9 | 27.5 |
| E | ±36, −15 | 224 | 7.7 | 9.4 | 40.9 |
| F | ±24, −31 | 221 | 7.1 | 7.5 | 48.0 |
| G | ±21, −32 | 192 | 6.7 | 6.1 | 54.3 |

TABLE 2

| | Location of 424 | Impedance (ohms) | Min. Power Efficiency (V/m)/Watt | | |
|---|---|---|---|---|---|
| | | | RV | Septum | LV |
| A | 0, −40 | 216 | 15.3 | 8.9 | 12.1 |
| B | −10, −29 | 224 | 15.5 | 9.4 | 9.4 |
| C | −19, −33 | 224 | 15.0 | 8.1 | 5.1 |
| D | −27, −30 | 222 | 13.8 | 7.4 | 3.7 |
| E | −34, −20 | 217 | 12.7 | 6.7 | 2.5 |

TABLE 3

| | Size of 422 (mm) | Impedance (ohms) | Min. Power Efficiency (V/m)/Watt | | |
|---|---|---|---|---|---|
| | | | RV | Septum | LV |
| A | 5 | 231 | 11.0 | 10.9 | 16.8 |
| B | 10 | 218 | 11.6 | 13.2 | 21.3 |
| C | 20 | 200 | 17.7 | 16.4 | 16.6 |
| D | 5 | 231 | 9.6 | 10.9 | 27.5 |
| E | 10 | 208 | 10.4 | 10.7 | 20.0 |
| F | 20 | 205 | 13.1 | 13.2 | 18.6 |

TABLE 4

| | Electrode Used | Impedance (ohms) | Min. Power Efficiency (V/m)/Watt | | |
|---|---|---|---|---|---|
| | | | RV | Septum | LV |
| A | 440 | 159 | 4.2 | 12.5 | 19.1 |
| B | 438 | 155 | 8.1 | 26.0 | 20.3 |
| C | 436 | 158 | 15.7 | 20.8 | 22.1 |

TABLE 5

| | Electrodes Used | Impedance (ohms) | Min. Power Efficiency (V/m)/Watt | | |
|---|---|---|---|---|---|
| | | | RV | Septum | LV |
| A | 448, 450 | 141 | 17.8, .2 | 19.9 | 17.4 |
| B | 452, 454 | 131 | .08 | 12.5 | 15.3 |
| C | 452, 454 | 129 | .08 | 16.7 | 14.8 |

TABLE 6

| Location of 424, 422 | Impedance (ohms) | Min. Power Efficiency (V/m)/Watt | | |
|---|---|---|---|---|
| | | RV | Septum | LV |
| A | ±40, 0 | 258 | 6.3 | 2.0 | 6.0 |
| B | ±40, 0 | 264 | 6.5 | 13.8 | 10.6 |
| C | ±39, −6 | 194 | 8.1 | 19.6 | 15.1 |
| D | ±40, 0 | 123 | 14.7 | 18.4 | 9.5 |
| E | ±40, 0 | 127 | 8.2 | 16.3 | 15.3 |
| F | ±39, −6 | 96 | 8.9 | 17.8 | 18.7 |

TABLE 7

| Spacing of 528, 428 | Impedance (ohms) | Min. Power Efficiency (V/m)/Watt | | |
|---|---|---|---|---|
| | | RV | Septum | LV |
| A | 34 | 200 | .06 | 34 | 23.2, 8.9 |
| B | 20 | 211 | .6 | 35.4 | 20.1 |
| C | 20 | 116 | — | .2 | 10.2 |

TABLE 8

| Size of 524, 526, 528 (mm) | Impedance (ohms) | Min. Power Power Efficiency (V/m)/Watt | | |
|---|---|---|---|---|
| | | RV | Septum | LV |
| A | 10, 5.5 | 328 | 18.5 | 18.5 | 14.8, 2.7 |
| B | 20, 10, 10 | 262 | 20.0 | 20.0 | 20.0, 5.8 |

TABLE 9

| Location of 534, 536 | Impedance (ohms) | Min. Power Efficiency (V/m)/Watt | | |
|---|---|---|---|---|
| | | RV | Septum | LV |
| A | ±23, −35 | 241 | 13.8 | 25.1 | 25.1, 7.7 |
| B | ±15, −37 | 245 | 13.5 | 27.3 | 14.5 |
| C | ±15, −37 | 258 | 6.2 | 12.4 | 10.0 |
| D | 10, −39 −38, −15 | 257 | 7.7 | 15.4 | 16.2, 5.6 |

TABLE 10

| | Impedance (ohms) | Min. Power Efficiency (V/m)/Watt | | | |
|---|---|---|---|---|---|
| | | RV | Septum | LV | LVA |
| A | 151 | 38.8 | 17.1 | 2.6 | 75.2 |
| B | 145 | 30.7 | 20.0 | 5.0 | 1.0 |

In conjunction with the above description, I claim:

1. A method of applying energy to a human heart, comprising:
    inserting a first electrode lead having an elongated first electrode adjacent a distal end of said lead into the coronary sinus and great vein of said heart such that said elongated electrode extends into the great vein of said heart;
    applying a second electrode to the right ventricle of said heart; and
    delivering electrical energy to said heart, via said first and second electrodes.

2. A method according to claim 1 wherein said step of applying said second electrode comprises transvenously inserting an elongated second electrode lead having an elongated second electrode into the right ventricle of said heart.

3. A method according to claim 2 wherein said second electrode lead is provided with a J-shaped curve adjacent its distal end and wherein said second elongated electrode is located along said J-shaped curve.

4. A method according to claim 3 wherein said step of inserting said second electrode lead comprises inserting said second electrode lead such that said J-shaped curve is located in the vicinity of the right ventricular apex of said heart.

5. A method according to claim 1, 2, 3 or 4 wherein said step of inserting said first electrode lead comprises inserting said first electrode lead into said coronary sinus and said great vein such that said first elongated electrode is located entirely within said coronary sinus and said great vein of said heart.

6. A method of applying energy to a human heart, comprising:
    inserting a first electrode lead having an elongated first electrode located in the vicinity of a distal end of said electrode lead into the coronary sinus and great vein of said heart such that said elongated electrode extends into the great vein of said heart and such that said first elongated electrode is located entirely within the great vein and coronary sinus of said heart;
    inserting a second electrode lead having a second elongated electrode into the right ventricle of said heart; and
    delivering electrical energy to said heart by means of said first and second elongated electrodes.

7. A method according to claim 1 or claim 6 wherein said step of inserting said first electrode lead comprises inserting a first electrode lead having a reduced diameter segment at its distal end, said elongated first electrode extending over said reduced diameter segment, such that said first electrode lead passes through the atrium of said human heart and into the coronary sinus of said human heart with said reduced diameter segment located in said great vein.

8. A method according to claim 7 wherein said elongated first electrode extends proximal to said reduced diameter segment and wherein said first electrode lead is located such that said elongated first electrode does not extend into the atrium of said human heart.

9. A method according to claim 1 or claim 6, further comprising the step of inserting a third electrode lead bearing a third electrode into the right atrium of said heart such that said third electrode is located in the right atrium of said heart and wherein said step of delivering electrical energy to said human heart comprises delivering electrical energy via said third electrode.

* * * * *